US00PP22606P3

(12) United States Plant Patent
Zaiger et al.

(10) Patent No.: US PP22,606 P3
(45) Date of Patent: Mar. 27, 2012

(54) PEACH TREE NAMED 'ZEE PRIDE'

(50) Latin Name: *Prunus perscia*
Varietal Denomination: Zee Pride

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/804,447

(22) Filed: Jul. 22, 2010

(65) Prior Publication Data

US 2012/0023629 P1 Jan. 26, 2012

(51) Int. Cl.
*A01H 5/00* (2006.01)

(52) U.S. Cl. ..... Plt./197

(58) Field of Classification Search ..... Plt./197
See application file for complete search history.

*Primary Examiner* — Kent L Bell

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Being a regular and productive bearer of large size fruit.
3. Fruit with a high degree of attractive red skin color.
4. Fruit with good flavor and eating quality, a good balance between acid and sugar.
5. Fruit with good storage and handling quality.

1 Drawing Sheet

Botanical classification: *Prunus persica.*

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach and proprietary trees, which are known to us, and mentioned herein, 'Vista' Peach (U.S. Plant Pat. No. 9,549), 'Sierra Rich' Peach (U.S. Plant Pat. No. 12,391), 'Country Sweet' Peach (U.S. Plant Pat. No. 11,090) and proprietary peach selections with field identification numbers '175LE263', '374LH329' and '57EE22'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was originated by us in our experimental orchard located near Modesto, Calif. as a first generation cross between two proprietary selected peach seedlings with field identification numbers (175LE263) and (374LH329). The seed parent (175LE263) originated from a first generation cross of 'Vista Rich' Peach (U.S. Plant Pat. No. 9,549) and the proprietary seedling (57EE22). The pollen parent originated from a first generation cross between 'Sierra Rich' Peach (U.S. Plant Pat. No. 12,391) and 'Country Sweet' Peach (U.S. Plant Pat. No. 11,090). A large number of these first generation seedlings were grown and budded on older 'Nemaguard' Rootstock (non-patented) to accelerate rapid fruit production for evaluation. Under close and careful observation we recognized the desirable tree and fruit characteristics of the present variety and selected it in 1999 for further asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree (*Prunus persica*) is of large size, vigorous, upright growth and a productive and regular bearer of large size, firm, yellow flesh, clingstone fruit with good flavor and eating quality. The fruit is further characterized by ripening in the early maturity season, having an attractive red skin color and being relatively uniform in size throughout the tree. In comparison to its maternal parent (175LE263) the tree of the new variety has approximately 150 hours higher winter chilling requirement and the fruit is 10 days earlier in maturity. In comparison to its pollen parent (374LH329) the tree of the new variety has approximately 200 hours higher winter chilling requirement with fruit maturing 7 days earlier, with firmer flesh, greater handling and shipping qualities. In comparison to the commercial peach variety 'Sierra Rich' (U.S. Plant Pat. No. 12,391) the fruit of the new variety has darker red skin color and matures approximately 20 days earlier.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from an 8 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 8 year old specimens grown near Modesto, Calif., with color in accordance with Munsell Book of Color.

Tree:

*Size.*—Large, pruned to 3 to 3.5 meters in height and width for economical harvesting of fruit. Varies with different cultural practices.

*Vigor.*—Vigorous, growth of approximately 1.5 to 2 meters in height the first growing season. Varies with soil type and fertility and climatic conditions.

*Form.*—Upright, usually pruned to vase shape.

*Branching habit.*—Upright, crotch angle approximately 30°, increases with heavy crop load.

*Productivity.*—Productive, fruit thinning and spacing necessary for desired market size fruit.

*Bearer.*—Regular, adequate fruit set 6 consecutive years. No alternate bearing observed.

*Fertility.*—Self-fertile.

*Density.*—Medium dense, usually pruned to vase shape which allows more sunlight to center of tree to enhance fruit color and health of fruit wood.

*Hardiness.*—Hardy in all fruit growing areas of California. Tree grown in USDA Hardiness Zone 9. Winter chilling requirement approximately 850 hours at or below 45° F.

Trunk:

*Size.*—Large. Average circumference 50.8 cm at 25.8 cm above ground on an 8 year old tree.

*Stocky.*—Medium.

*Texture.*—Medium shaggy, roughness increases with age.

*Color.*—Varies from 7.5YR 2/4 to 2.5Y 7/2.

Branches:

*Size.*—Medium size. Average circumference 31.8 cm at 1.2 meters above ground. Crotch angle approximately 30°, increases with crop load.

*Surface texture.*—New growth relatively smooth. Mature growth medium rough, roughness increases with age.

*Lenticels.*—Average number 30 in a 25.8 sq cm area. Average length 6.2 mm. Average width 2.3 mm. Color varies from 10YR 7/6 to 10YR 6/6.

*Color.*—New growth varies from 5GY 6/6 to 5GY 6/8 with 7.5R 4/6 where exposed to the sun. Old growth varies from 10YR 3/4 to 2.5Y 3/4, varies with age of growth.

Leaves:

*Size.*—Large. Average length 148.4 mm. Average width 40.8 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins. Lower surface relatively smooth with small ridges created by midrib an pinnate venation. Both upper and lower surfaces glabrous.

*Petiole.*—Average length 9.6 mm. Average width 1.6 mm. Longitudinally grooved. Surface — glabrous. Color varies from 5GY 4/6 to 5GY 4/8.

*Glands.*—Type — reniform. Size — large. Average length 1.4 mm. Average diameter 1.0 mm. Number varies from 4 to 7, average number 5. Located primarily on the base of the leaf blade and upper portion of the petiole. Color varies from 2.5GY 5/6 to 5GY 6/6.

*Stipules.*—None present.

*Color.*—Upper surface varies from 5GY 4/6 to 7.5GY 3/6. Lower surface varies from 5GY 4/4 to 7.5GY 4/4. Midvein color varies 2.5GY 7/6 to 5GY 7/8.

Flower buds:

*Size.*—Large. Average length 19.5 mm. Average diameter 12.3 mm.

*Hardiness.*—Hardy with respect to California winters.

*Form.*—Plump, conical, becoming elongated before opening.

*Pedicel.*—Average length 4.6 mm. Average width 2.3 mm. Color varies from 2.5GY 6/8 to 10Y 7/6.

*Color.*—Varies from 7.5RP 6/12 to 5RP 8/6.

Flowers:

*Blooming period.*—Date of First Bloom Feb. 25, 2010. Date of Petal Fall Mar. 8, 2010, varies slightly with climatic conditions.

*Size.*—Large, showy. Average height 20.3 mm. Average diameter 51.2 mm.

*Petals.*—Normally 5, alternately arranged to sepals. Size — large. Average length 25.2 mm. Average width 26.5 mm. Form — orbicular, narrows slightly at point of attachment. Margin — sinuate. Color varies from 7.5RP 8/6 to 5RP 8/4. Both upper and lower surfaces glabrous.

*Sepals.*—Normally 5, alternately arranged to petals. Size — large. Average length 7.2 mm. Average width 7.1 mm. Shape — triangular, apex rounded. Margin — entire. Surface — upper surface glabrous, lower surface pubescent. Color — upper surface varies from 2.5GY 5/8 to 5GY 6/6. Lower surface varies from 5R 2/4 to 7.5R 2/6.

*Stamens.*—Average number per flower 47. Average filament length 15.8 mm. Filament color varies from N 9.5/ (white) to 7.5RP 8/4. Anther color varies from 7.5R 4/10 to 5R 3/8.

*Pollen.*—Self-fertile. Color varies from 2.5Y 7/10 to 5Y 7/10.

*Pistil.*—Normally 1. Surface — pubescent. Average length 19.3 mm. Position of stigma even with anthers. Color varies from 10Y 8/6 to 2.5GY 8/6.

*Fragrance.*—Wanting.

*Color.*—Varies from 5RP 8/6 to 7.5RP 8/4.

*Number flowers per flower bud.*—One.

*Pedicel.*—Average length 4.8 mm. Average width 2.4 mm. Color varies from 10Y 7/6 to 2.5GY 7/6.

Fruit:

*Maturity when described.*—Firm ripe.

*Date of first picking.*—Jun. 5, 2010.

*Date of last picking.*—Jun. 14, 2010, varies slightly with climatic conditions.

*Size.*—Large. Average diameter axially 67.0 mm. Average transversely in suture plane 74.3 mm. Average weight 227.8 grams, average weight varies slightly with fertility of the soil, amount of thinning and climatic conditions.

*Form.*—Globose.

*Suture.*—Nearly smooth, extends from base to apex.

*Ventral surface.*—Relatively smooth.

*Apex.*—Rounded to very slight tip.

*Base.*—Varies from flat to slightly retuse.

*Stem cavity.*—Rounded to slightly elongated in the suture plane. Average depth 6.8 mm. Average diameter 10.2 mm.

Stem:

*Size.*—Medium. Average length 9.3 mm. Average diameter 4.5 mm.

*Color.*—Varies from 2.5GY 6/8 to 5GY 6/8.

Flesh:

*Ripens.*—Fairly even, only slightly earlier at the apex.

*Texture.*—Firm, meaty.

*Fibers.*—Few, small and tender.

*Firmness.*—Very firm, comparable to the commercial peach variety 'Sierra Rich' (U.S. Plant Pat. No. 12,391).

*Aroma.*—Moderate.

*Amydgalin.*—Undetected.

*Eating quality.*—Good.

*Flavor.*—Good, good balance between acid and sugar.

*Juice.*—Moderate, enhances flavor.

*Brix.*—Average Brix 11.5°, varies slightly with amount of fruit per tree and climatic conditions.

*Color.*—Varies from 2.5Y 8/8 to 2.5Y 8/10 with 7.5R 4/10 in areas of flesh.

*Pit cavity.*—Large. Average length 44.2 mm. Average width 30.6 mm. Average depth 11.2 mm. Color varies from 7.5Y 8.5/4 to 7.5Y 7/6.

Skin:

*Thickness.*—Medium.

*Surface.*—Smooth.

*Pubescence.*—Moderate amount, very short.

*Tendency to crack.*—None.

*Color.*—Ground color varies from 2.5Y 8.5/6 to 5Y 8/6. Overspread with 7.5R 4/8 to 7.5R 3/6.

*Tenacity.*—Tenacious to flesh.

*Astringency.*—Undetected.

Stone:

*Type.*—Clingstone.

*Size.*—Large. Average length 43.8 mm. Average width 30.2 mm. Average thickness 21.9 mm.

*Form.*—Obovoid.

*Base.*—Flat.

*Apex.*—Pointed. Average length 2.3 mm.

*Surface.*—Pitted throughout, pits vary from round to elongated.

*Sides.*—Unequal, one side extending further from the suture plane.

*Ridges.*—Relatively smooth, extending from base to apex.

*Tendency to split.*—None.

*Color.*—Varies from 10YR 6/6 to 10YR 6/8, when dry.

Kernel:

*Size.*—Large. Average length 20.0 mm. Average width 13.4 mm. Average depth 5.4 mm.

*Form.*—Ovate.

*Viability.*—Viable.

*Skin.*—Color varies from 5Y 9/4 to 7.5Y 9/4.

Use: Dessert.

*Market.*—Local and long distance.

Keeping quality: Good, held firm in cold storage at 38° to 42° F. for two weeks without internal breakdown or appreciable loss of flavor.

Shipping quality: Good, minimal skin scarring or bruising of flesh during picking, packing or shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. The present new variety of peach tree (*Prunus persica*) substantially as illustrated and described.

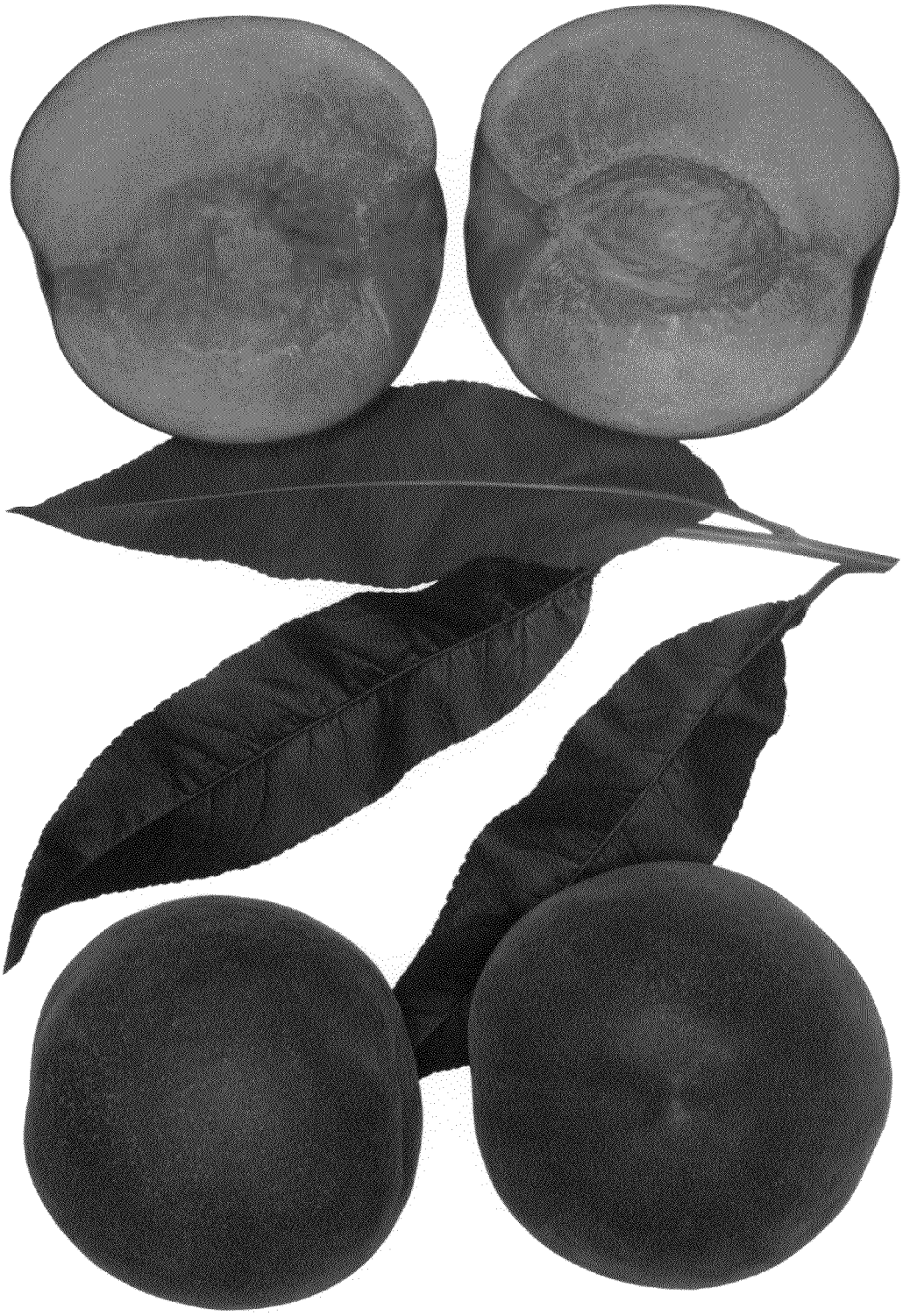

* * * * *